(12) United States Patent
Nogueira et al.

(10) Patent No.: US 12,253,399 B2
(45) Date of Patent: Mar. 18, 2025

(54) MULTIPHASE FLOWMETERS AND RELATED METHODS

(71) Applicant: Schlumberger Technology Corporation, Sugar Land, TX (US)

(72) Inventors: Felipe Nogueira, Singapore (SG); Cheng-Gang Xie, Singapore (SG); Kun Yang, Singapore (SG); Arifin Arifin, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/464,387

(22) Filed: Sep. 11, 2023

(65) Prior Publication Data
US 2023/0417589 A1    Dec. 28, 2023

Related U.S. Application Data

(63) Continuation of application No. 16/523,042, filed on Jul. 26, 2019, now Pat. No. 11,808,615.
(Continued)

(51) Int. Cl.
*G01F 1/74*    (2006.01)
*G01F 1/66*    (2022.01)
(Continued)

(52) U.S. Cl.
CPC ............. *G01F 1/74* (2013.01); *G01F 1/666* (2013.01); *G01F 1/86* (2013.01); *G01N 27/10* (2013.01);
(Continued)

(58) Field of Classification Search
CPC .. G01F 1/74; G01F 1/666; G01F 1/86; G01N 27/10; G01N 2011/0073; G01N 29/02
See application file for complete search history.

(56) References Cited

U.S. PATENT DOCUMENTS 4,240,287 A * 12/1980 Mast .................. G06M 11/00
                                                                73/152.18
5,654,551 A    8/1997 Watt
(Continued)

FOREIGN PATENT DOCUMENTS

CN    103399025    11/2013
CN    103697950    4/2014
(Continued)

OTHER PUBLICATIONS

Al-Khamis et al., Evaluation of PhaseWatcher Multiphase Flow Meter (MPFM) Performance in Sour Environments, May 5-8, 2008, Offshore Technology Conference, OTC 19152, pp. 1-6 (Year: 2008).*
(Continued)

*Primary Examiner* — Mi'Schita' Henson
(74) *Attorney, Agent, or Firm* — Jeffrey D. Frantz

(57) ABSTRACT

Multiphase flowmeters and related methods are disclosed herein. An example apparatus includes a flowmeter and a fluid conduit to provide a flow path for a fluid relative to the flowmeter. The example apparatus includes a sensor coupled to the fluid conduit to generate data indicative of at least one of a presence, an absence, or a mass flow rate of solids in the fluid during flow of the fluid through the fluid conduit. The example apparatus includes a processor. The sensor is to be communicatively coupled to the processor. The processor is to selectively determine flow rates for one or more phases of the fluid based on data generated by the flowmeter and a first algorithmic mode or a second algorithmic mode selected based on the sensor data.

19 Claims, 9 Drawing Sheets

Related U.S. Application Data

(60) Provisional application No. 62/703,466, filed on Jul. 26, 2018.

(51) Int. Cl.
  G01F 1/86 (2006.01)
  G01N 27/10 (2006.01)
  G01N 33/28 (2006.01)
  G01N 11/00 (2006.01)

(52) U.S. Cl.
  CPC . G01N 33/2847 (2013.01); *G01N 2011/0073* (2013.01)

(56) References Cited

U.S. PATENT DOCUMENTS

| | | |
|---|---|---|
| 6,405,604 B1 | 6/2002 | Berard |
| 7,105,805 B2 | 9/2006 | Berard |
| 7,676,344 B2 | 3/2010 | Chevalier |
| 8,472,582 B2 | 6/2013 | Roux |
| 8,521,436 B2 | 8/2013 | Agar |
| 8,739,635 B2 | 6/2014 | Bruno |
| 8,855,263 B2 | 10/2014 | Roux |
| 9,995,725 B2 | 6/2018 | Arifin |
| 10,054,537 B2 | 8/2018 | Arifin |
| 10,605,075 B2 | 3/2020 | Suheil |
| 10,732,017 B2 | 8/2020 | Wang |
| 2007/0287190 A1 | 12/2007 | Chevalier |
| 2010/0140496 A1 | 6/2010 | Pinguet |
| 2010/0280757 A1 | 11/2010 | Agar |
| 2013/0319132 A1 | 12/2013 | Lupeau |
| 2014/0121970 A1* | 5/2014 | Ljungdahl ................ G01F 1/86 702/6 |
| 2014/0238116 A1 | 8/2014 | Kwan |
| 2015/0346117 A1 | 12/2015 | Nyfors |
| 2016/0238422 A1 | 8/2016 | Wee |
| 2016/0245684 A1 | 8/2016 | Wee |
| 2017/0122085 A1 | 5/2017 | Suheil |
| 2017/0284853 A1 | 10/2017 | Ahmad |
| 2018/0010429 A1 | 1/2018 | Willberg |
| 2020/0003599 A1 | 1/2020 | Theuveny |

FOREIGN PATENT DOCUMENTS

| | | | | |
|---|---|---|---|---|
| CN | 204115788 U | * | 1/2015 | ............... G01F 1/66 |
| CN | 105239993 | | 1/2016 | |
| CN | 207554022 | | 6/2018 | |
| CN | 207554022 U | * | 6/2018 | ......... E21B 41/0099 |
| EP | 3299576 | | 3/2018 | |
| GB | 2400436 | | 10/2004 | |
| WO | 03087735 | | 10/2003 | |
| WO | 2009082758 | | 7/2009 | |
| WO | 2011119045 | | 9/2011 | |
| WO | 2014122093 | | 8/2014 | |
| WO | WO-2014122093 A1 | * | 8/2014 | ............... G01F 1/58 |
| WO | 2015019081 | | 2/2015 | |
| WO | 2015142610 | | 9/2015 | |
| WO | 2018160927 | | 9/2018 | |
| WO | 2019120261 | | 6/2019 | |

OTHER PUBLICATIONS

Padsalgikar, "Particle Transport in Stratified Gas-Liquid-Solid Flow", 2015, UMI Dissertaion Publishing, ProQuest LLC, UMI 3715140, 195 pages (Year: 2015).*

Fiore et al., "Improving Multiphase Flowmeter Accuracy for Hydrocarbon Allocation and Wet Gas Production of Unconventional Oil-Gas Wells", 2024, International Petroleum Technology Conference, IPTC-239342-MS, pp. 1-17, DOI 10.2523/IPTC-23942-MS (Year: 2024).*

Alali et al., "Auto-Correction Algorithm of Multiphase Flowmeter Water Cut Measurements in Undersaturated Oil Wells", 2023, Society of Petroleum Engineers, SPE-214450-MS, pp. 1-9, DOI 10.2118/214450-MS (Year: 2023).*

Al-Lababidi et al., "Upstream Multiphase Flow Assurance Monitoring Using Acoustic Emission", 2012, Acoustic Emission, Dr. Wojciech Sikorski (Ed.), ISBN 978-953-51-0056-0, pp. 217-250 (Year: 2012).*

Mohammed N. Al-Khamis et al., Evaluation of PhaseWatcher Mulitphase Flow Meter (MPFM) Performance in Sour Environments, 2008, Offshore Technology Conference OTC 19152, pp. 1-6 (Year: 2008).

Office Action issued in Chinese Patent Appl. No. CN201910682818.9 on Nov. 7, 2023; 18 pages (with English translation).

Notification of the Decision to Grant issued in Chinese Patent Appl. No. CN201910682818.9 on Sep. 4, 2024; 8 pages (with English translation).

* cited by examiner

MULTIPHASE FLOWMETERS AND RELATED METHODS

CROSS-REFERENCE TO RELATED APPLICATIONS

This patent application is a continuation of U.S. patent application Ser. No. 16/523,042, filed Jul. 26, 2019, which claims the benefit of United States Provisional Patent Application Ser. No. 62/703,466, filed Jul. 26, 2018. Each of the above applications is expressly incorporated herein by reference in its entirety.

BACKGROUND

This disclosure relates generally to flowmeters and, more particularly, to multiphase flowmeters and related methods.

DESCRIPTION OF THE RELATED ART

Management of solid (e.g., sand production, fracturing proppant flow back) in the oil and gas production industry is an ongoing concern because solids can damage production equipment. For example, even small amounts of sand can cause erosion over time when fluid flow velocities are high and excessive flow back of proppant solids can cause adverse damage to fractured rock formation. Accordingly, monitoring for sand or proppants can provide information about the onset of solid production and/or an amount of solid produced as part of characterizing fluid flows, maintaining production equipment, and the productivity of fractured shale oil-gas wells.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

An example apparatus includes a flowmeter and a fluid conduit to provide a flow path for a fluid relative to the flowmeter. The example apparatus includes a sensor coupled to the fluid conduit to generate data indicative of at least one of a presence, an absence, or a mass flow rate of solids in the fluid during flow of the fluid through the fluid conduit. The example apparatus includes a processor. The sensor is to be communicatively coupled to the processor. The processor is to selectively determine flow rates for one or more phases of the fluid based on data generated by the flowmeter and a first algorithmic mode or a second algorithmic mode selected based on the sensor data.

An example method includes selecting a first algorithmic mode or a second algorithmic mode based on a phase composition of a multiphase fluid flowing through a fluid conduit. In the example method, the selection is based on sensor data generated during flow of the fluid through the conduit. The sensor data is indicative of at least one of a presence, an absence, or a mass flow rate of solids in the fluid. The example method includes determining flow rates of one or more phases of the fluid based on the selected first algorithmic mode or the selected second algorithmic mode.

Another example apparatus includes a flowmeter to generate fluid flow data during flow of a multiphase fluid through a conduit. The example apparatus includes means for detecting solids in the fluid. The means for detecting is to generate sensor data during the flow of the fluid through the conduit. The example apparatus includes a processor to select one of a first algorithmic mode or a second algorithmic mode to determine flow rates of one or more phases of the fluid based on the sensor data.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended to familiarize the reader with certain aspects and contexts of some embodiments without limitation to the claimed subject matter.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
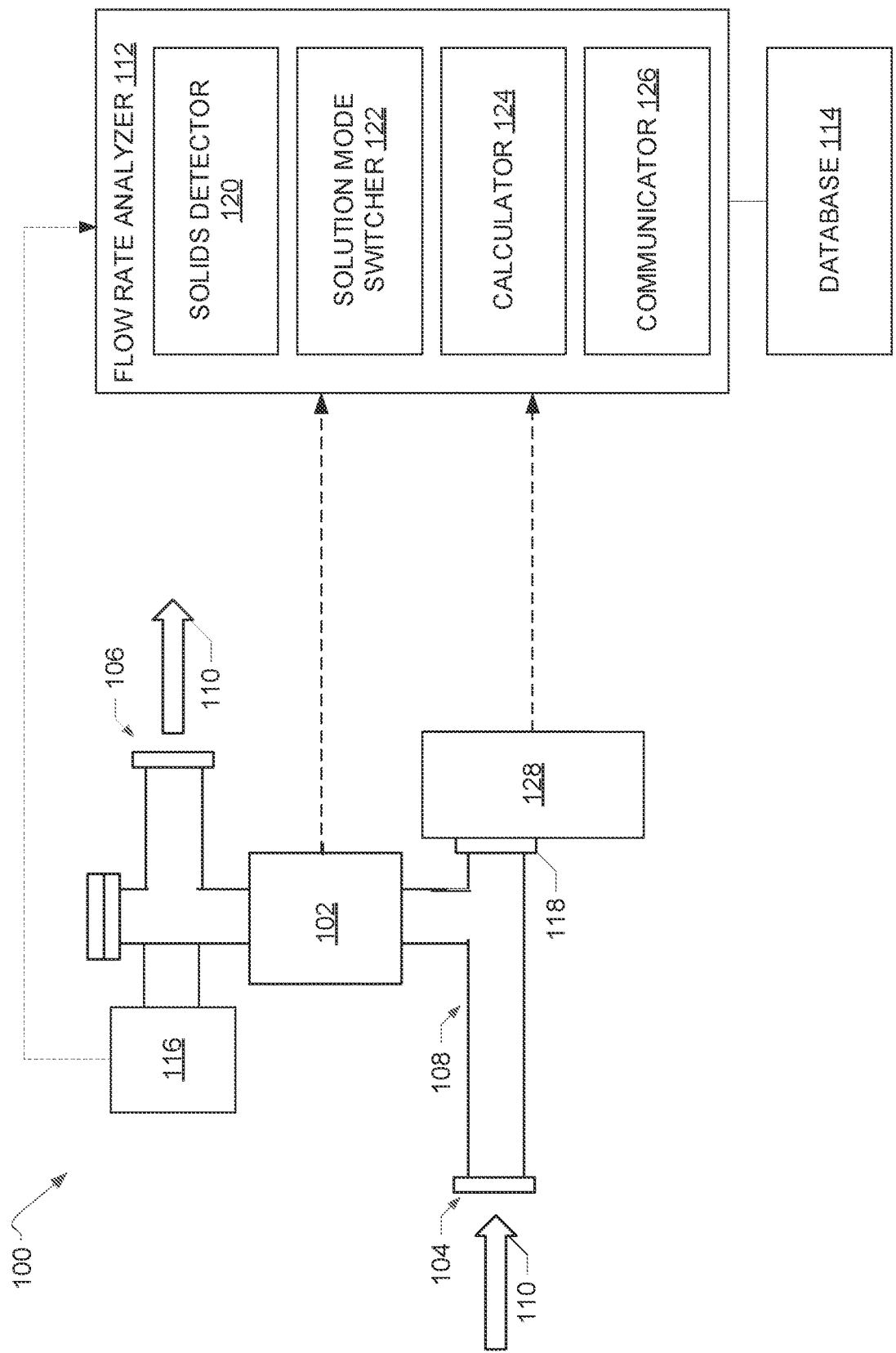
FIG. 1 illustrates an example system including a flow rate analyzer for analyzing multiphase fluid flows in accordance with teachings of this disclosure.

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," and "the" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

In the oil and gas production industry, multiphase flowmeters (e.g., multi-energy gamma ray based flowmeters) are used to monitor individual phases of a multiphase fluid flow including, for example, oil, water, and gas phases. In some instances, the multiphase flow can include four phases, namely, water/brine; oil; gas; and solids such as sand, proppants, and/or drill-out debris. In the context of reservoir characterization and production testing, misrepresentations with respect to detection of solids in the fluid flow can adversely affect the accuracy of measurements obtained from data collected by the flowmeters. In the context of post-hydraulic fracturing operations such as frac-plug drill-out, clean-up, and/or frac flow back, multiphase proppant (e.g., sand) monitoring is performed to verify that the amount of proppant produced from the well is within a predefined operating envelope to prevent damage to the frac job, which can occur when significant amounts of proppants are mobilized from a near-wellbore region of the well. However, although three-phase multiphase flowmeters known in the art can provide measurements for oil, water, and gas flow rates, such known flowmeters may fail to provide accurate flow rates for each phase in instances when the flow has four phases.

Disclosed herein are example systems and methods that provide for measurements of four-phase flow rates for a flow including oil, water/brine, gas, and solids (e.g., sand). Examples disclosed herein use, for example, multi-energy gamma ray and venturi-based multiphase flowmeters capable of analyzing three-phase flows in combination with a solid detection sensor (e.g., a conductivity probe, a piezoelectric sensor) to detect at least one of (a) a presence or an absence or (b) a flow rate (i.e., a mass flow rate) of solids such as sand at different flow intervals. Based on the presence, the absence, or the mass flow rate of solids at a given time, examples disclosed herein selectively employ different algorithms to determine individual flow rates for either a three-phase flow or a four-phase flow. In examples disclosed herein, when no solids or substantially no solids are detected in the flow, an Oil-Water-Gas (OWG) linear attenuation solution triangle of a multi-energy gamma ray and venturi-based flowmeter is used to determine oil, water, and gas flow rates. Conversely, when solids are detected in the flow, examples disclosed herein automatically adjust or switch the algorithmic mode used to determine flow rates. In such examples, a Sand-Liquid-Gas (SLG) linear attenuation solution triangle of the multi-energy gamma ray and venturi based flowmeter is used to determine sand, liquid (water and oil), and gas flow rates for the four-phase flow.

The phase composition of the fluid flow evolves throughout workflows occurring at the well. For example, during a frac-plug drillout and frac flow back workflows, fluid flows in which four phases are simultaneously present typically occur during the frac clean-up stages. In such stages, the water-liquid ratio (WLR) varies at a relatively slow and predictable rate. Further, during the frac clean-up states, solids in the flow may be present as discrete sand slugs, and interleaved with periods of sand-free flow. Based on these understandings of flow composition and fluid behavior at different workflow states, examples disclosed herein capitalize on the capabilities of multi-energy gamma ray based three-phase flowmeters to measure water, oil, and gas phases. In particular, examples disclosed herein extend the capabilities of the three-phase flowmeters to four-phase flows based on the detection of solids in the flow and the automatic switching between the OWG and SLG solution triangles. Some examples disclosed herein further determine fluid flow properties such as WLR and/or solid-to-liquid ratios.

Also disclosed herein are example sand detectors that can be disposed in a flow path of a fluid conduit for direct or substantially direct engagement with, for instance, sand in the fluid flow. Example sand detectors disclosed herein include piezoelectric acoustic sensor(s) to detect impact of the sand on the detector during the fluid flow. Data generated by example sand detectors disclosed herein can be used to detect at least one of (a) the presence or the absence or (b) the mass flow rate of sand in the fluid flow and to adjust the algorithmic mode (e.g., the OWG or SLG solution triangles) used to determine individual flow rates accordingly.

FIG. 1 illustrates an example system 100 for determining individual phase flow rates at different flow intervals for fluid flow including three phases (e.g., oil, water, and gas) and four phases (e.g., sand, liquid, gas, where liquid includes oil and water). The example system 100 includes a multi-phase flowmeter (MPFM) 102. The MPFM 102 is, for example, based on multi-energy gamma-ray transmission attenuation and venturi differential pressure measurements. The MPFM 102 measures individual phase flow rates of well fluids (e.g., gas, oil, water) flowing between an inlet 104 and a fluid conduit outlet 106 of a fluid conduit 108, as represented by arrows 110 of FIG. 1. In the example of FIG. 1, data generated by the MPFM 102 is transmitted (e.g., via one or more wired or wireless communication protocols) to a flow rate analyzer 112. The MPFM data is stored in a database 114, which may be located at the flow rate analyzer 112 or located elsewhere and in communication with the flow rate analyzer 112.

The example system 100 of FIG. 1 includes means for detecting solids, such as sand, in the fluid flow. In the example of FIG. 1, the means for detecting solids includes one or more solid detection sensors 116. The solid detection sensor(s) 116 can include piezoelectric acoustic sensors that are coupled to the fluid conduit 108 at one or more locations such as near the fluid conduit outlet 106. In some examples, the example system 100 may include other sensors such as a water conductivity sensor 128. The water conductivity sensor 128 can include microwave sensor(s) that are coupled to the fluid conduit 108 at one or more locations, such as at a blind-tee inlet 118 (e.g., an end flange) of the fluid conduit 108. The solid detection sensor(s) 116 and/or the water conductivity sensor 128 can collect data during the flow periodically, aperiodically, substantially continuously, etc. For example, the solid detection sensor(s) 116 and/or the water conductivity sensor 128 can collect data every second during the fluid flow. The data generated by the solid detection sensor(s) 116 and/or the water conductivity sensor 128 is transmitted to the flow rate analyzer 112 and stored in the database 114.

The example flow rate analyzer 112 of FIG. 1 selectively determines individual phase flow rates based on at least one of the presence or the absence, or the mass flow rate of solids in the fluid flow, or based on changes of conductivity (e.g., salinity) of water in the fluid flow. In the example of FIG. 1, data collected by the solid detection sensor(s) 116 and/or the water conductivity sensor 128 is used by the flow rate analyzer 112 to determine the presence of solids or the salinity value of water in the fluid flow and to dynamically adjust the algorithms employed by the flow rate analyzer 112 to determine one or more fluid properties for the flow, such as individual phase flow rates, WLR, and/or a solids-in-liquid ratio (SLR).

The example flow rate analyzer 112 of FIG. 1 includes a solids detector 120. The solids detector 120 analyzes the data received from the solid detection sensor(s) 116. Based on the analysis of the data, the solids detector 120 identifies whether or not the fluid flow contains solids in a particular time interval. The solids detector 120 can detect the presence of solids in the fluid flow based on the sensor data satisfying one or more predefined thresholds with respect to, for instance, amplitude of the signal data generated by the piezoelectric acoustic sensors.

The example flow rate analyzer 112 includes a solution mode switcher 122 and a calculator 124. In the example of FIG. 1, if the solids detector 120 determines that no solids (e.g., sand) are present in the fluid flow, the solution mode switcher 122 determines that the calculator 124 should use an Oil-Water-Gas (OWG) solution triangle to measure oil, gas, and water flow rates in the three-phase fluid flow. If the solids detector 120 determines that solids are present in the fluid flow, the solution mode switcher 122 determines that the calculator 124 should use a Sand-Liquid-Gas (SLG) solution triangle to measure flow rates of sand, liquid (water and oil), and gas for the four-phase flow. At a later time, if the solids detector determines that solids are no longer present in the fluid flow, the solution mode switcher 122 determines that the calculator 124 is to return to using the OWG solution triangle, as the fluid flow can be characterized as a three-phase flow. Thus, the solution mode switcher 122 automatically switches the algorithmic mode used by the calculator 124 to determine fluid phase flow rates based the presence or absence of solids in the fluid flow. The calculator 124 can use the water conductivity (salinity) data provided by water conductivity sensor 128 to verify the accuracy of the determination of the WLR and the flow rates of the fluid phase in examples where there is a significant change in the water salinity when using the OWG or SLG solution triangles.

The calculator 124 determines the individual phase flow rates using the OWG solution triangle or the SLG solution triangle as selected by the solution mode switcher 122. As disclosed herein, the OWG solution triangle and the SLG solution triangle can provide reference points for analyzing the behavior of the phases of the fluid flow. In some examples, the calculator 124 also determines one or more fluid properties such as WLR and SLR.

The example flow rate analyzer 112 includes a communicator 126. The communicator 126 can transmit one or more outputs generated by the calculator 124 (e.g., WLR, SLR, flow rates) for presentation via, for instance, a display screen in communication with the flow rate analyzer 112. The outputs can be displayed in textual and/or visual (e.g., graphical) form.

Figure 3:
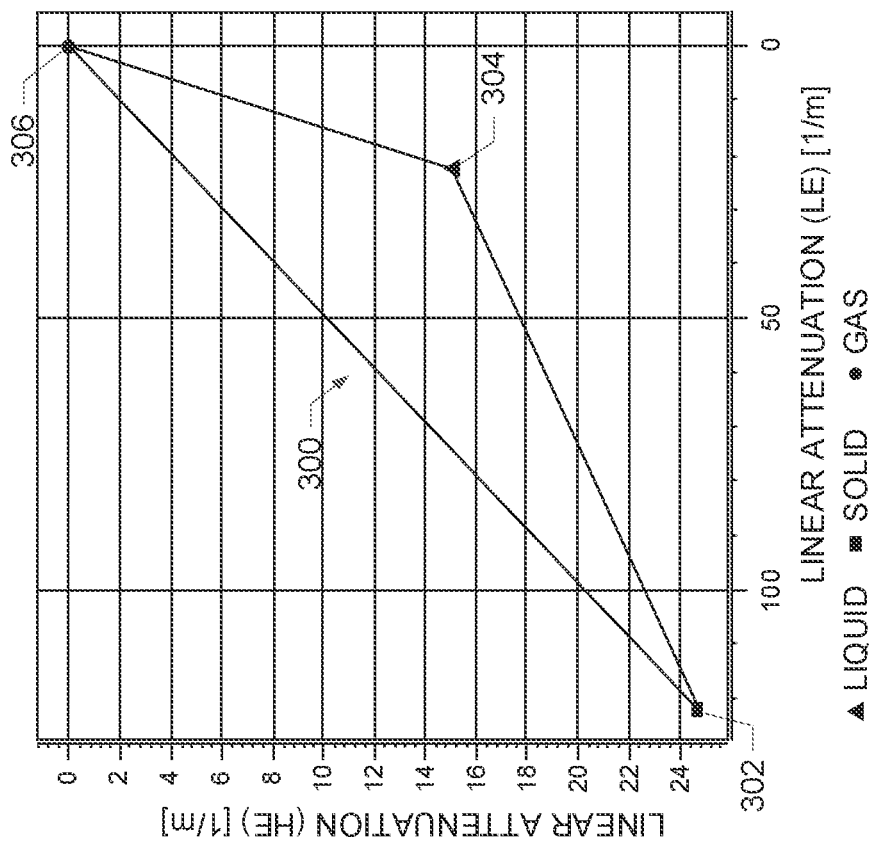
FIG. 3 is an example graph of a solid-liquid-gas linear attenuation triangle that may be implemented by the example flow rate analyzer of FIG. 1.
Figure 2:
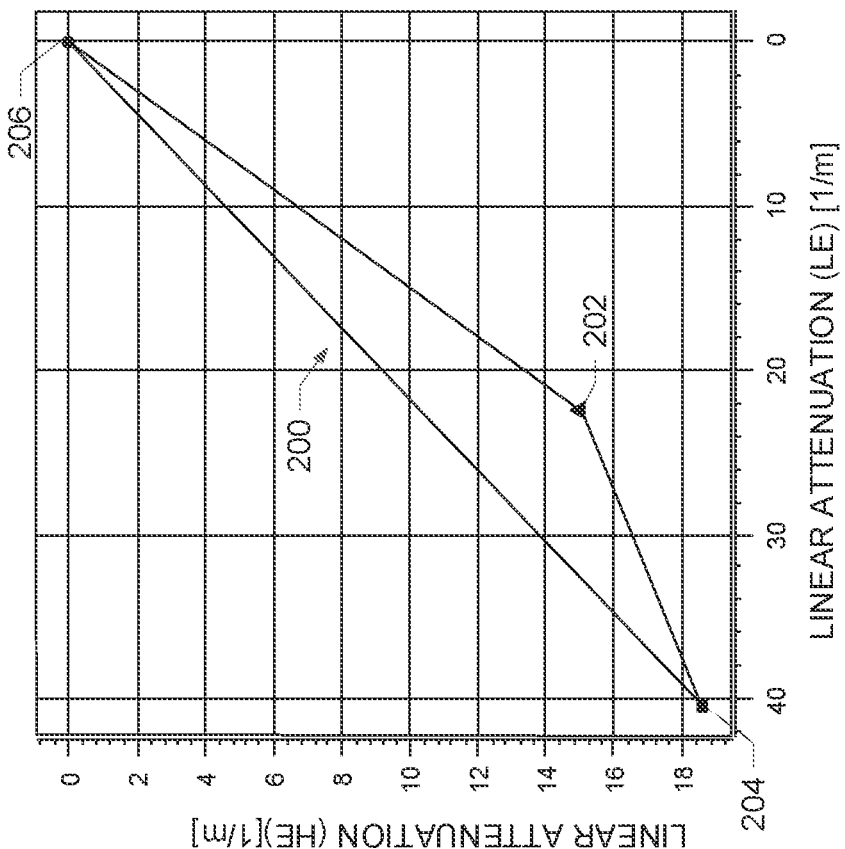
FIG. 2 is an example graph of an oil-water-gas linear attenuation triangle that may be implemented by the example flow rate analyzer of FIG. 1.

FIG. 2 is graphical depiction of an example OWG linear attenuation solution triangle 200 that is used by the calculator 124 of the example flow rate analyzer 112 of FIG. 1 when determining individual phase flow rates for a three-phase fluid flow including oil, water, and gas. FIG. 3 is a graphical depiction of an example SLG linear attenuation solution triangle 300 that is used by the calculator 124 of the flow rate analyzer 112 of FIG. 1 when determining individual phase flow rates for a four-phase fluid flow including solids, liquid (i.e., oil and water), and gas. Gamma ray attenuation MPFMs (e.g., the MPFM 102 of FIG. 1) measure gamma rays passing through a fluid in a fluid conduit (e.g., the fluid conduit 108 of FIG. 1). The attenuation of the gamma rays is affected by the phase composition of the fluid. In the graphs of FIGS. 2 and 3, the x-axis represents low energy (LE) linear attenuation of gamma rays passing through fluid and the y-axis represents high energy (HE) linear attenuation of gamma rays passing through the fluid.

Referring to FIG. 2, an envelope for the OWG solution triangle 200 can be defined over a range of water-in-liquid ratio (WLR) values by an oil operating point 202, a water operating point 204, and a gas operating point 206. Similarly, an envelope for the SLG solution triangle 300 of FIG. 3 can be defined by a solid operating point 302, a liquid operating point 304, and a gas operating point 306. The operating points for the respective phases can be based on calibration data for corresponding single phase fluids. In examples in which a significant change in water salinity occurs, the water operating point 204 or the liquid operating point 304 can be automatically recalibrated based on the water salinity data provided by the water conductivity sensor 128 of FIG. 1.

In the example of FIG. 3, the liquid operating point 304 in the SLG solution triangle 300 can be determined in substantially real-time based on (a) an analysis of water and oil at a proportion of a last known WLR value for a three-phase fluid flowing through the fluid conduit 108 and associated with the OWG solution triangle 200 and (b) an assumption that a change in WLR when solids (e.g., sand) are present is substantially negligible. To compute the liquid operating point 304, the following computations can be performed by the example calculator 124 of the flow rate analyzer 112. An in-situ analysis of a sand and water mixture in the MPFM 102 of FIG. 1 yields a linear attenuation coefficient for the mixture $\lambda_{mix}$ based on a Beer-Lambert equation:

$\lambda_{mix} = \lambda_s \alpha_s + \lambda_w \alpha_w$ (Eq. 1), where $\alpha$ is a linear fraction equal to a volume fraction given constant beam cross-section area. Equation 1 can be rearranged to solve for a sand linear attenuation coefficient $\lambda_s$:

$$\lambda_s = \frac{\lambda_{mix} - \lambda_w \alpha_w}{\alpha_s}. \quad \text{(Eq. 2)}$$

A porosity (volumetric ratio) of the sand during in-situ can be expressed as $$\Phi = \frac{V_w}{V_s + V_w} = \alpha_w = (1 - \alpha_s). \quad \text{(Eq. 3)}$$

Accordingly, the sand linear attenuation coefficient $\lambda_s$ can be expressed in terms of porosity as follows:

$$\lambda_s = \frac{\lambda_{mix} - \lambda_w \Phi}{(1 - \Phi)}, \quad \text{(Eq. 4)}$$

where $\lambda_{mix}$ is determined from the sand and water mixture in-situ, water linear attenuation coefficient $\lambda_w$ is initially determined from water in-situ, and $\Phi$ is determined from, for example, known data obtained during lab measurements. As the specific gravity for sand $p_s$ is known, the mass attenuation of sand can be calculated as follows:

$$\mu_s = \frac{\lambda_{mix} - \lambda_w \Phi}{\rho_s (1 - \Phi)}. \quad \text{(Eq. 5)}$$

Equation 5 applies for a single energy window of the MPFM 102 of FIG. 1. The MPFM 102 can be associated with one or more energy windows (e.g., a first energy window EW1, a second energy window EW2, an $n^{th}$ energy window EW_N, etc.) for radioactive elements or artificial sources. In some examples, the energy windows include a low energy window (LE), a high energy window (HE), and a very high energy window (VHE) for, for instance, a radioactive element. In some such examples, each of the MPFM's low energy, high energy and very high energy windows is a combination of several emissions of an isotope (such as barium $^{133}$Ba, with LE=32, HE=81, VHE=356 kiloelectron volts (keV)). Accordingly, Equation 5 can be used as a first degree approximation as follows:

$$\mu_{s,e} \approx \frac{\lambda_{mix,e} - \lambda_{w,e} \Phi}{\rho_s (1 - \Phi)} \text{ where } e \in \{LE, HE, VHE\}(keV), \quad \text{(Eq. 6)}$$

The foregoing analysis also applies to brine water if the same brine water used for the water point in-situ is also used in a sand and brine mixture in-situ. A change in brine salinity can be measured using the brine water conductivity (salinity) sensor 128 to automatically adjust the values $\lambda_{w,e}$ and $\rho_w$ for brine water.

In the foregoing analysis, because the linear attenuation coefficients for water and oil $\lambda_w$ and $\lambda_o$ are obtained from water in-situ (and $\lambda_w$ can be auto-adjusted by the salinity value measured by the water conductivity sensor 128) and oil in-situ, a composite liquid linear attenuation can be expressed as:
$\lambda_L = \lambda_w \cdot (WLR) + \lambda_o \cdot (1-WLR)$ (Eq. 7). The calculation of mass attenuation of the composite liquid can be defined as follows:

$$\mu_L = \frac{\lambda_w \cdot (WLR) + \lambda_o \cdot (1 - WLR)}{\rho_L}, \text{ where} \quad \text{(Eq. 8)}$$

$$\rho_L = \rho_w \cdot (WLR) + \rho_0 \cdot (1 - WLR). \quad \text{(Eq. 9)}$$

Based on the foregoing equations, the calculator 124 of the example flow rate analyzer 112 of FIG. 1 can determine the fractions of solids, liquid and gas and their ratios such as solids-to-liquid ratio (SLR) using the SLG solution triangle.

Figure 4:
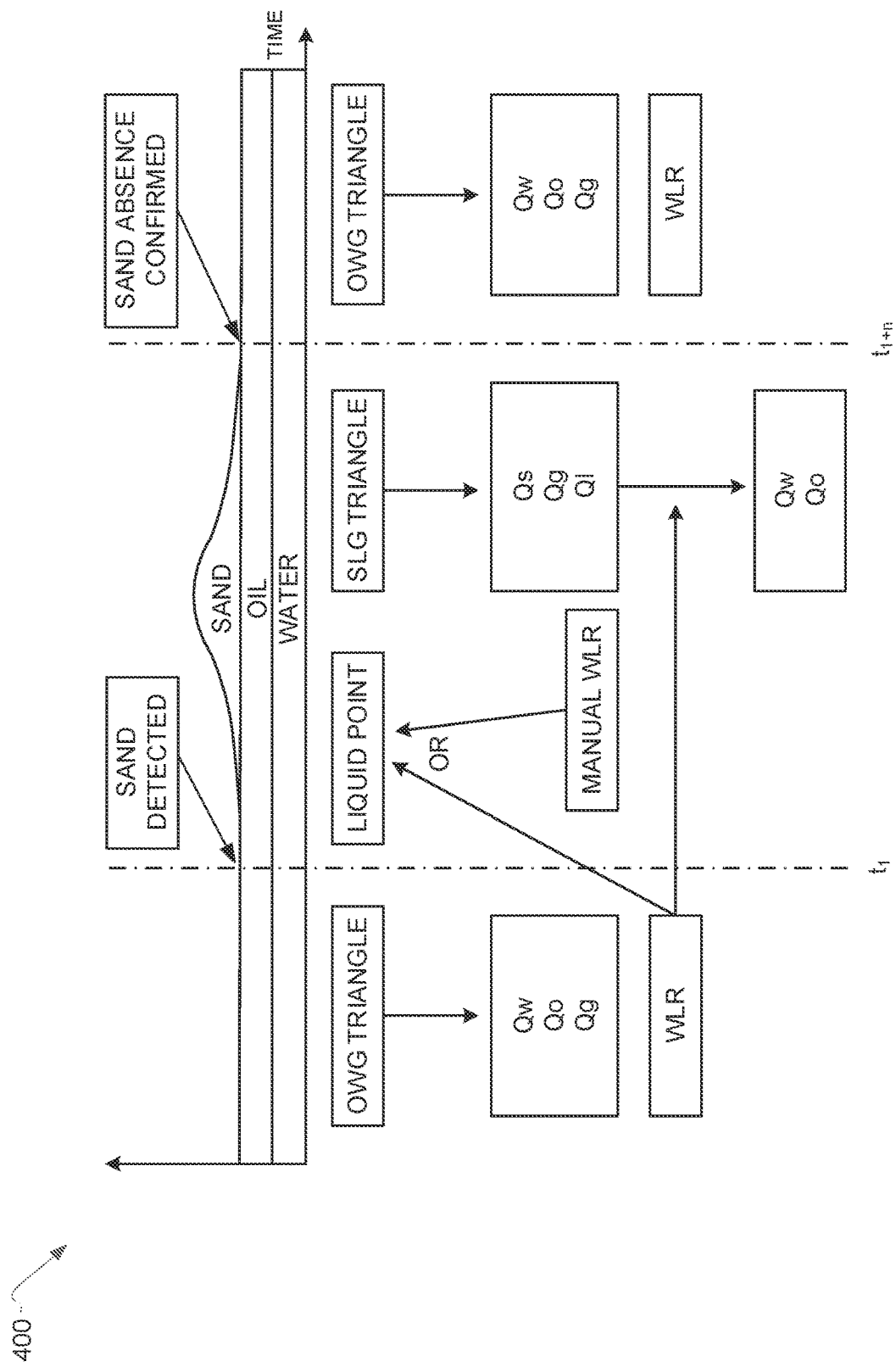
FIG. 4 is a diagram of an example process for analyzing multiphase fluid flows in accordance with teachings of this disclosure.

FIG. 4 is a diagram 400 of an example process for analyzing multiphase fluid flows in accordance with teachings of this disclosure. In particular, the diagram 400 of FIG. 4 illustrates the switching between algorithmic modes (e.g., the OWG solution triangle 200, the SLG solution triangle 300) by the example solution mode switcher 122 of the flow rate analyzer 112 of FIG. 1. As disclosed above, the solution mode switcher 122 instructs the calculator 124 to use a particular solution triangle based on the presence, the absence, or the mass flow rate of solids (e.g., sand) in the fluid flow as detected by the solids detector 120.

As shown in FIG. 4, at a time before time $t_1$, the flow contains substantially no sand and, thus, the solution mode switcher 122 instructs the calculator 124 to determine a water flow rate value $Q_w$, an oil flow rate value $Q_o$, and a gas flow rate value $Q_g$ based on the OWG solution triangle and the data generated by the multi-energy gamma-ray based MPFM 102. In the example of FIG. 4, the calculator 124 also calculates the WLR value based on the data generated by the MPFM 102 for the three-phase flow. The calculator 124 can use the data generated by the water conductivity sensor 128 to verify an accuracy of the calculation of the WLR value in examples in which there is a significant water salinity change.

In the example of FIG. 4, at time $t_1$, the solids detector 120 detects the presence of sand in the flow based on data from the solid detection sensor(s) 116. Accordingly, the solution mode switcher 122 determines that the calculator 124 should use the SLG solution triangle to calculate individual phase flow rates for the four-phase fluid. The solution mode switcher 122 instructs the calculator 124 to use the SLG solution triangle to calculate the flow rates of the solids ($Q_s$), gas ($Q_g$), and liquid (oil and water) ($Q_l$). In some examples, the solid detection sensor(s) 116 may provide an independent solids mass flow rate measurement.

As illustrated in FIG. 4, in some examples, the WLR value calculated by the calculator 124 using the OWG solution triangle is used by the calculator 124 to determine the liquid point in the SLG solution triangle. The calculator 124 can use the data from the water conductivity sensor 128 to verify an accuracy of the determination of the liquid point in the SLG solution triangle in examples in which there is a significant water salinity change. Thus, in such examples, the calculator 124 uses the last known WLR value as measured when sand is absent from the flow. This use of the last known WLR value is based on an assumption that changes in WLR values are negligible during intervals where sand is present as compared to intervals where sand is absent. As shown in FIG. 4, in some other examples, the WLR value is provided as a manual input received by the flow rate analyzer 112.

The calculator 124 uses the SLG solution triangle to determine a sand flow rate value $Q_s$, a gas flow rate value $Q_g$, and a liquid flow rate value $Q_l$. The calculator 124 uses the liquid flow rate value a and the WLR value for the period of time when the sand was absent from the flow to calculate a water flow rate value $Q_w$ and an oil flow rate value $Q_o$ for the flow during the time period in which sand is present in the flow. Thus, the calculator 124 determines individual phase flow rates for four-phase flows. The example system 100 of FIG. 1 thereby extends the capabilities of the MPFM 102 with respect to analyzing multiphase fluids.

At some time after time $t_1$, e.g., time $t_{1+n}$ in FIG. 4, the solids detector 120 determines that sand is substantially absent in the flow based on data received from the solid detection sensor(s) 116. Accordingly, the solution mode switcher 122 instructs the calculator 124 to return to using the OWG solution triangle. As during the time interval prior to time $t_1$, the calculator 124 uses the OWG solution triangle to calculate a water flow rate value $Q_w$, an oil flow rate value $Q_o$ and a gas flow rate value $Q_g$ for the three-phase flow. The calculator 124 also calculates the WLR value for the flow in the current time interval, which may also be used in future calculations when solids are detected in the flow again. The calculator 124 can use the data generated by the water conductivity sensor 128 to verify an accuracy of the calculation of the WLR value in examples in which there is a significant water salinity change.

As disclosed above with respect to FIG. 1, solids such as sand can be detected in a fluid flow based on data generated by the solid detection sensor(s) 116. Also, data generated by the water conductivity sensor 128 for detecting brine/water salinity can be used to verify the accuracy of the determination of WLR and fluid phase flow rate(s) (which can include the flow rate of the solids). In some other examples disclosed herein, a piezoelectric sand detector can be disposed in the fluid conduit 108 to detect sand in the fluid flow.

Figure 5:
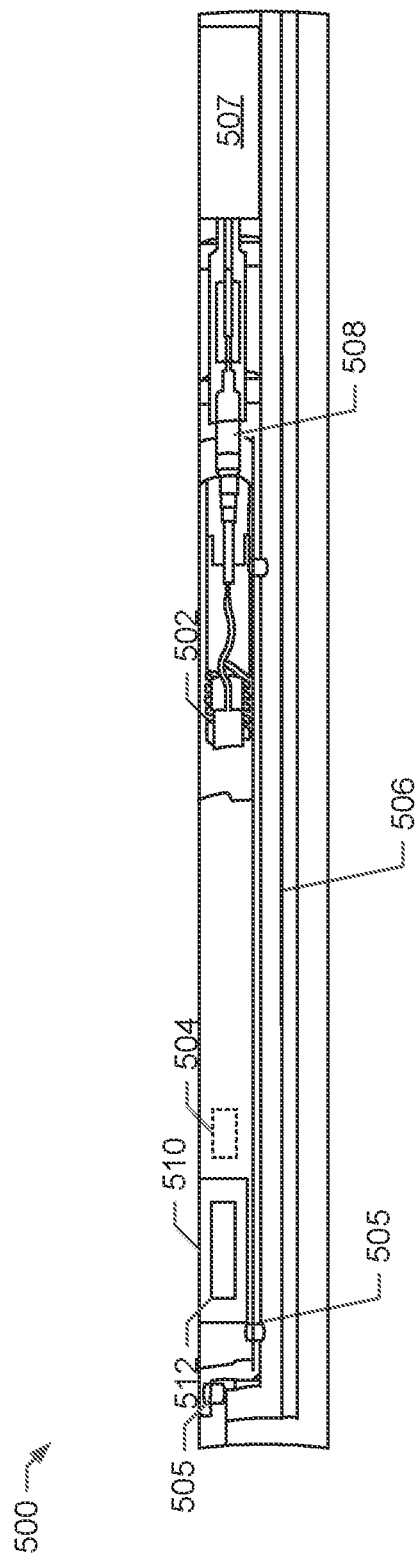
FIG. 5 illustrates an example sand detector in accordance with teachings of this disclosure.

FIG. 5 illustrates an example sand detector 500 that can be disposed in a fluid conduit, such as the fluid conduit 108 of FIG. 1. The example sand detector 500 includes a piezoelectric (acoustic) sensor 502 disposed in a detector body 504. The detector body 504 and the piezoelectric sensor 502 are supported by a mandrel 506. The detector body 504 is mechanically isolated via, for example, one or more elastomers 505 disposed between the detector body 504 and the mandrel 506 to reduce mechanical noise. The piezoelectric sensor 502 is communicatively coupled to electronics 507 (e.g., a processor) via a coaxial cable 508. As disclosed below, the sand detector 500 can be implemented as part of a sand flowmeter that includes the electronics 507 for generating data in response to detection of sand by the piezoelectric sensor 502 as the sand hits the detector body 504.

In operation, the sand detector 500 may be exposed to high velocity multiphase flows containing sand and, as such, the sand detector 500 may be subject to erosion over time. In some examples, the detector body 504 includes a metal test piece 510 and a reference probe 512 coupled thereto. A baseline electrical resistance measurement through the metal test piece 510 on the detector body 504 can be collected prior to exposure of the sand detector 500 to fluid flow. Periodic or continuous electrical resistance measurements can be collected during fluid flow and analyzed (e.g., by the flow rate analyzer 112 of FIG. 1) to determine deviations from the baseline measurement, which can indicate metal loss arising from erosion.

Figure 6:
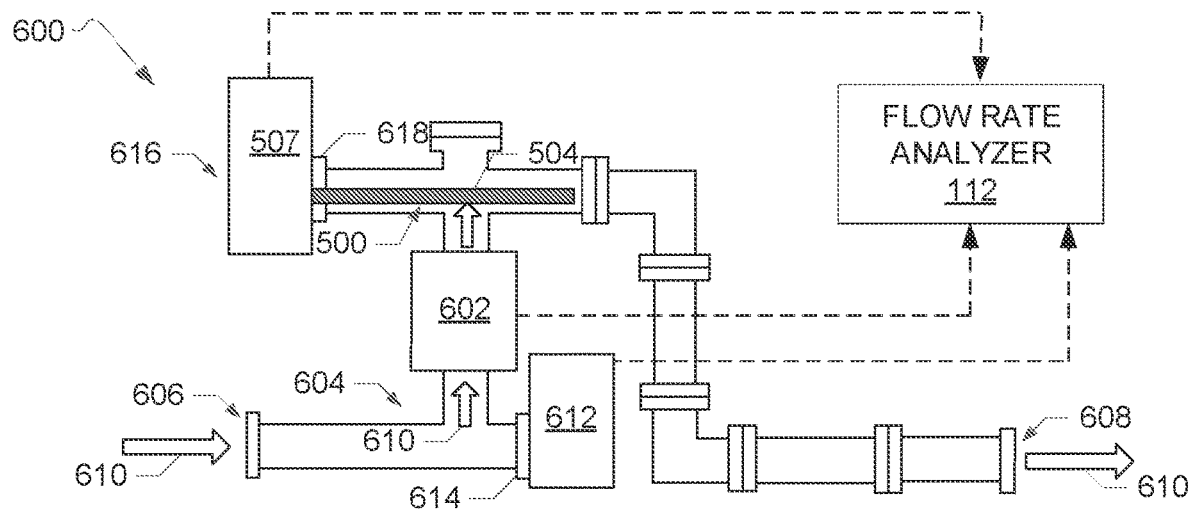
FIG. 6 illustrates an example system including the sand detector of FIG. 5 and the flow rate analyzer of FIG. 1.

FIG. 6 depicts a first example system 600 including a multi-phase flowmeter (MPFM) 602 and the example sand detector 500 of FIG. 5 coupled to a fluid conduit 604. The MPFM 602 measures flow rates of a multiphase fluid flowing between an inlet 606 and an outlet 608 of the fluid conduit 604 through which a multiphase fluid flows, as represented by arrows 610 of FIG. 6. The example system 600 includes a water conductivity sensor 612 coupled to the fluid conduit 604 at a first blind-tee inlet 614 (e.g., an end flange) of the fluid conduit 604. The water conductivity sensor 612 measures, for instance, changes in water salinity. Data generated by the MPFM 602 and the water conductivity sensor 612 is transmitted (e.g., via one or more wired or wireless communication protocols) for processing by the flow rate analyzer 112 of FIG. 1.

The example system 600 includes a sand flowmeter 616 including the sand detector 500 of FIG. 5. The sand flowmeter 616 is disposed a second blind-tee inlet 618 (e.g., an end flange) of the fluid conduit 604. As shown in FIG. 6, the sand detector 500 is disposed in the fluid conduit 604 (i.e., in a flow path of the fluid conduit 604) substantially perpendicular to a direction of the incoming fluid flow after exiting the MPFM 602. As a result, solids (e.g., sand) in the fluid flow have a direct or substantially direct impact on the detector body 504 of the sand detector 500.

Figure 7:
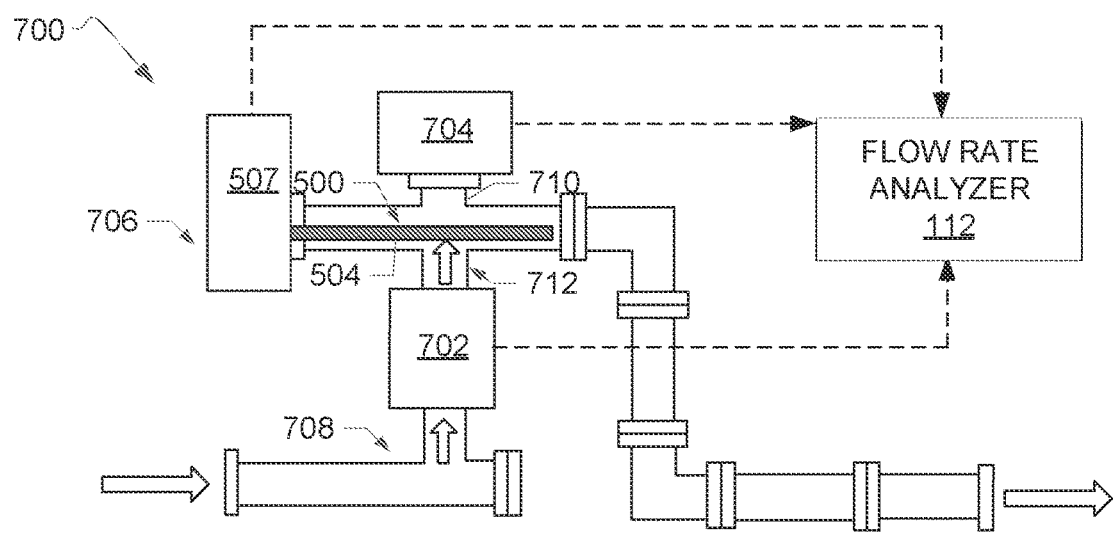
FIG. 7 illustrates another example system including the sand detector of FIG. 5 and the flow rate analyzer of FIG. 1.

FIG. 7 depicts a second example system 700 including a multiphase flowmeter (MPFM) 702, a water conductivity sensor 704, and a sand flowmeter 706 including the sand detector 500 coupled to a fluid conduit 708, substantially as disclosed above in connection with FIG. 6. As compared to the example of FIG. 6, in the example of FIG. 7, the water conductivity sensor 704 is coupled to a vertical (e.g., top) end flange 710 of the fluid conduit 708. In the example of FIG. 7, the water conductivity sensor 704 generates data after oil and water have mixed downstream of a vertical portion 712 of the fluid conduit 708. The data collected by the water conductivity sensor 704 can be used to determine WLR measurements in addition to salinity measurements. Also, the coupling of the water conductivity sensor 704 to the vertical end flange 710 reduces opportunities for sand build-up on a measurement surface of the water conductivity sensor 704 probe as fluid flows past the water conductivity sensor 704.

In the example systems 600, 700 of FIGS. 6 and 7, the sand detector 500 is positioned in the fluid conduit 604, 708 to encounter the fluid after the fluid exits the vertically installed MPFM 602, 702. Fluid flowing through the MPFM 602, 702, which can include a flow restriction device such as a venturi (e.g., for differential-pressure flowrate measurement) typically exhibits increased homogeneity as compared to fluid that has not yet passed through the MPFM 602, 702. Sand in less homogeneous fluid flows or flows may be difficult for the sand detector 500 to accurately detect because the sand grains may impact the sand detector 500 in non-representative manner. Accordingly, placing the sand detector 500 downstream of the MPFM 602, 702 results in improved detection of sand in the fluid flow as compared to if the sand detector 500 were positioned upstream of MPFM 602, 702. However, the example sand detector 500 can be positioned in the fluid conduit 604, 708 in other locations than shown in FIG. 6 and/or FIG. 7.

In the examples of FIGS. 6 and 7, data indicative of the detection of sand by the sand detector 500 (e.g., data generated by the piezoelectric sensor 502) is transmitted to the flow rate analyzer 112. The solid detector 120 (FIG. 1) of the flow rate analyzer 112 uses the sand detection data generated by the sand detector 500 to determine whether solids are present in the fluid flow or to determine sand mass flow rate. If solids are present in the fluid flow, the solid detector 120 communicates with the solution mode switcher 122 (FIG. 1) to adjust the three-phase or four-phase algorithmic mode (e.g., OWG or SLG solution triangles) used by the calculator 124 to calculate flow rates accordingly as disclosed above in connection with FIGS. 1-4.

In some examples, the detection of sand by the sand detector 500 of FIGS. 5-7 can be used by the flow rate analyzer 112 of FIGS. 1, 6, and 7 to adjust and/or correct oil, water, and gas flow rate measurements in the presence of sand when the sand concentration is too low for measurement via multiphase flow metering alone.

In some other examples, gas-volume fraction and flow velocity measurements from the MPFM 602, 702 can be used to automatically adjust signal amplification gain of the sand detector. The flow rate analyzer 112 may help amplify the sand detector signal data to account for whether the sand is being carried by gas- or liquid-dominant carrying fluid. For example, if sand is carried by a liquid-dominant flow, the sand detector signal data may need to be amplified because the sand does not impact the sand detector 500 as hard as when the sand is carried by a gas-dominant flow.

Laminar flows may result in a different detection response of the piezoelectric sand detector 500 as compared to turbulent flows. Accordingly, the example flow rate analyzer 112 of FIGS. 1, 6, and 7 can correct the effects of different flow regimes to provide for improved analysis of the data from the sand detector 500 indicative of the presence and mass flow rate of sand. For example, the calculator 124 of the flow rate analyzer 112 of FIGS. 1, 6, and 7 can use fluid characteristics such as Reynolds numbers to determine a degree of confidence with respect to the detection of sand. For a gas-liquid slug flow, slug flow characteristics can be used by the calculator 124 to determine a degree of confidence in the sand detection measurements.

As mentioned above, in cases of four-phase flows, the oil and water flow rates ($Q_w$ and $Q_o$) are determined based on WLR values entered manually or obtained from a MPFM measurement system, with the use of a water conductivity sensor that tracks changes in brine/water salinity to improve accuracy of the WLR measurements made by the MPFM in cases of varying water salinity. In examples where the WLR values are manually input, the calculator 124 of the flow rate analyzer 112 uses the manually input WLR value for calculations performed by the calculator 124 until the WLR value is manually updated. However, the WLR and water salinity values may change during workflows such as frac flow back. In the early phase of frac flow back, water salinity values are expected to rise rapidly for a short duration. WLR and salinity values are expected to decrease until reaching a stability period post-frac and then the WLR value may continuously increase during normal well production. For example, a well may start at 100% WLR post frac, finish at 30% WLR post frac-flowback, and then increase as well productivity decreases following the simulation in production via fracturing.

Figure 8:
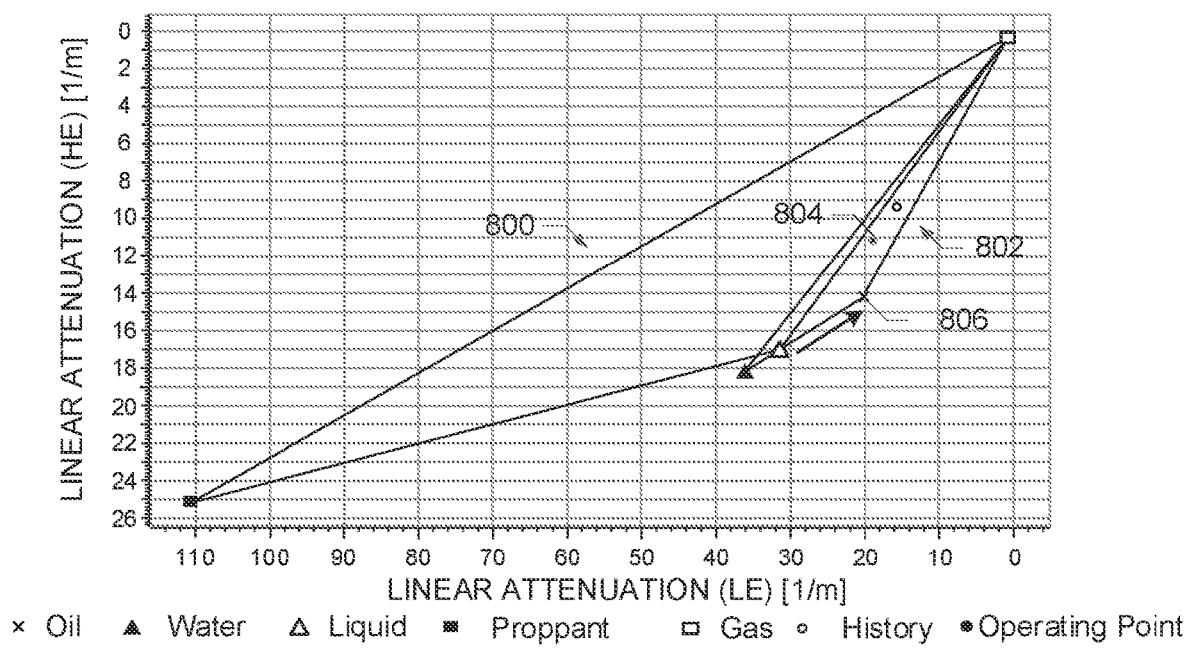
FIG. 8 is an example graph of a solid-liquid-gas linear attenuation triangle and an Oil-Water-Gas solution triangle in accordance with teachings of this disclosure.
Figure 9:
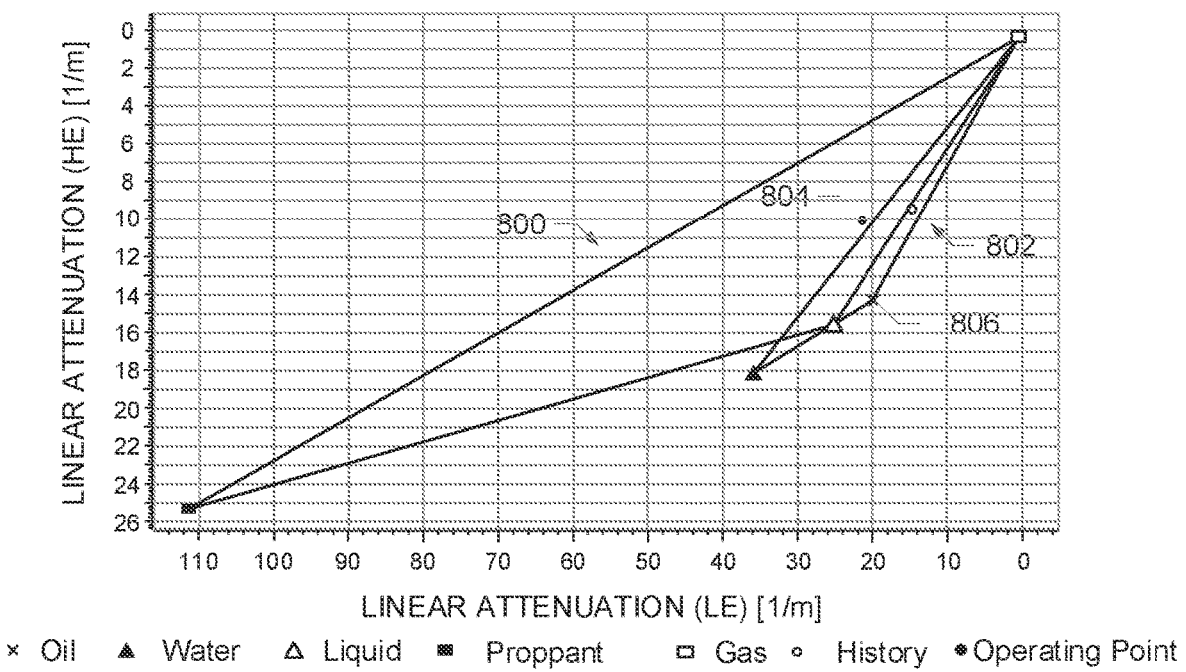
FIG. 9 is another example graph of a solid-liquid-gas linear attenuation triangle and an Oil-Water-Gas solution triangle in accordance with teachings of this disclosure.

To address the changes in WLR that may not be reflected in the manually input WLR value, the example flow rate analyzer 112 of FIG. 1 automatically updates the WLR value used in the calculation when solids are absent from the fluid flow (i.e., the manually input WLR value). FIG. 8 illustrates a graph including a SLG linear attenuation solution triangle 800 and an OWG linear attenuation solution triangle 802. In the example of FIG. 8, the apexes of the triangles 800, 802 represent 100% phase fraction for each individual phase (where liquid is considered a phase). In some examples, the actual WLR value may be lower than the manually input WLR value. When an operating point 804 is outside of the gas-liquid line in the SLG solution triangle 800, the solution mode switcher 122 of the flow rate analyzer 112 determines that the WLR has changed to include more oil and less water during periods of no solids. The calculator 124 automatically adjusts the fractions of oil and water to re-compute the WLR. Accordingly, the calculator 124 adjusts a liquid point 806 along the water-oil line of the OWG solution triangle 802. As shown in FIG. 9, as a result of the adjustment of the WLR value, the operating point 804 moves inside the SLG solution triangle 800. In other examples in which the operating point 804 is outside the solid-liquid line of the SLG solution triangle 800, the calculator 124 automatically increases the WLR value. As a result, the liquid point 806 moves toward the water point until the operation point 804 is inside the SLG solution triangle 800. The calculator 124 may perform several iterations with respect to adjusting the liquid point in the OWG solution triangle 802 or the SLG solution triangle 800 until the operating point falls inside the triangle(s).

While an example manner of implementing the flow rate analyzer 112 is illustrated in FIGS. 1, 6, and 7, one or more of the elements, processes and/or devices illustrated in FIGS. 1, 6, and/or 7 may be combined, divided, re-arranged, omitted, eliminated and/or implemented in any other way. Further, the example database 114, the example solids detector 120, the example solution mode switcher 122, the example calculator 124, the example communicator 126, and/or, more generally, the example flow rate analyzer 112 of FIGS. 1, 6, and/or 7 may be implemented by hardware, software, firmware and/or any combination of hardware, software and/or firmware. Thus, for example, any of the example database 114, the example solids detector 120, the example solution mode switcher 122, the example calculator 124, the example communicator 126, and/or, more generally, the example flow rate analyzer 112 of FIGS. 1, 6, and 7 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)), field programmable gate array(s) (FPGA(s)), and/or field programmable logic device(s) (FPLD(s)). When reading any of the apparatus or system claims of this patent to cover a purely software and/or firmware implementation, at least one of the example database 114, the example solids detector 120, the example solution mode switcher 122, the example calculator 124, the example communicator 126, and/or, more generally, the example flow rate analyzer 112 of FIGS. 1, 6, and/or 7 is/are hereby expressly defined to include a non-transitory computer readable storage device or storage disk such as a memory, a digital versatile disk (DVD), a compact disk (CD), a Blu-ray disk, etc. including the software and/or firmware. Further still, the example flow rate analyzer 112 of FIGS. 1, 6, and/or 7 may include one or more elements, processes and/or devices in addition to, or instead of, those illustrated in FIGS. 1, 6, and/or 7, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Figure 10A:
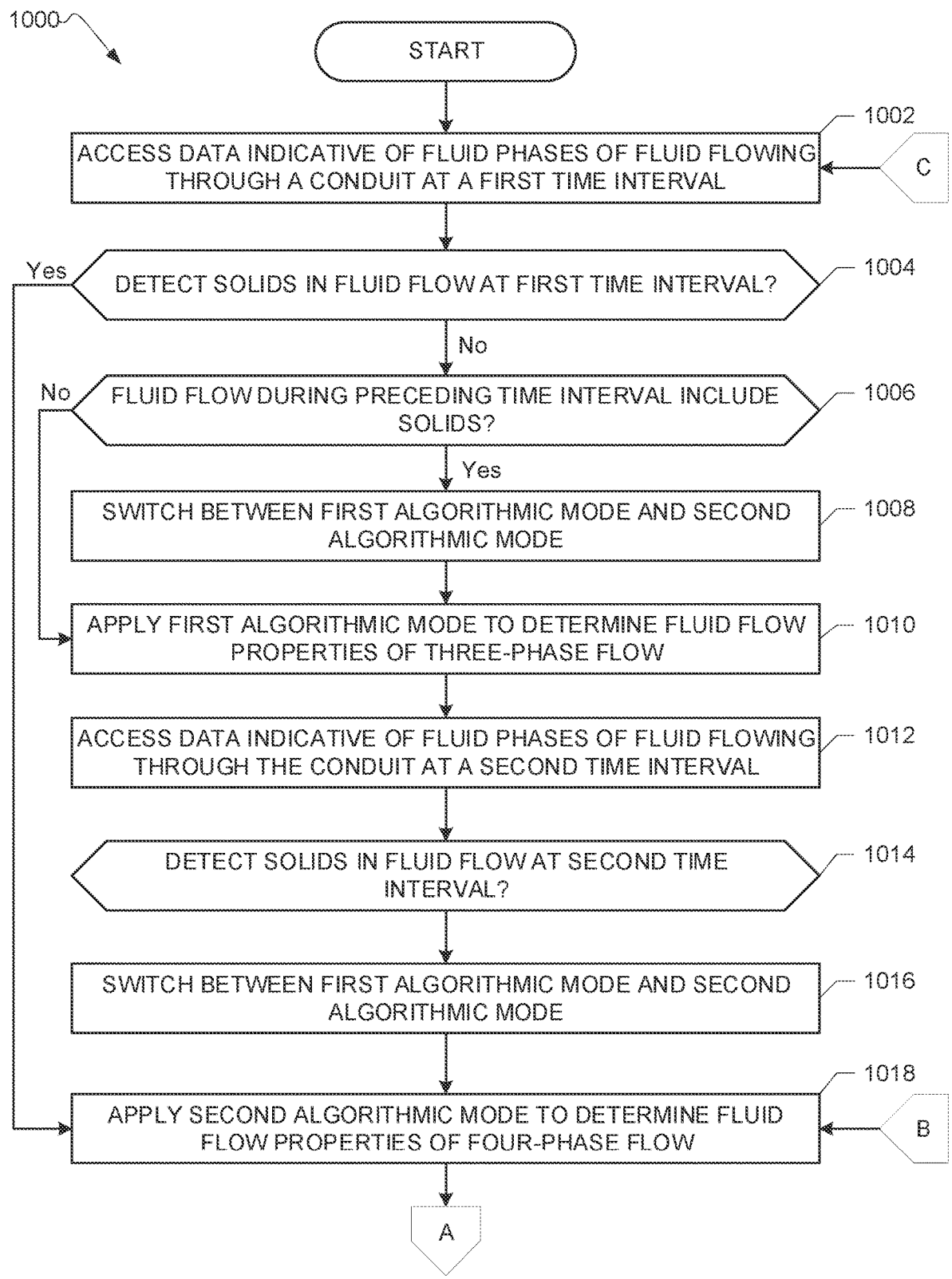
FIGS. 10A and 10B include a flowchart of an example method that may be executed to implement the example flow rate analyzer of FIGS. 1, 6, and/or 7.
Figure 10B:
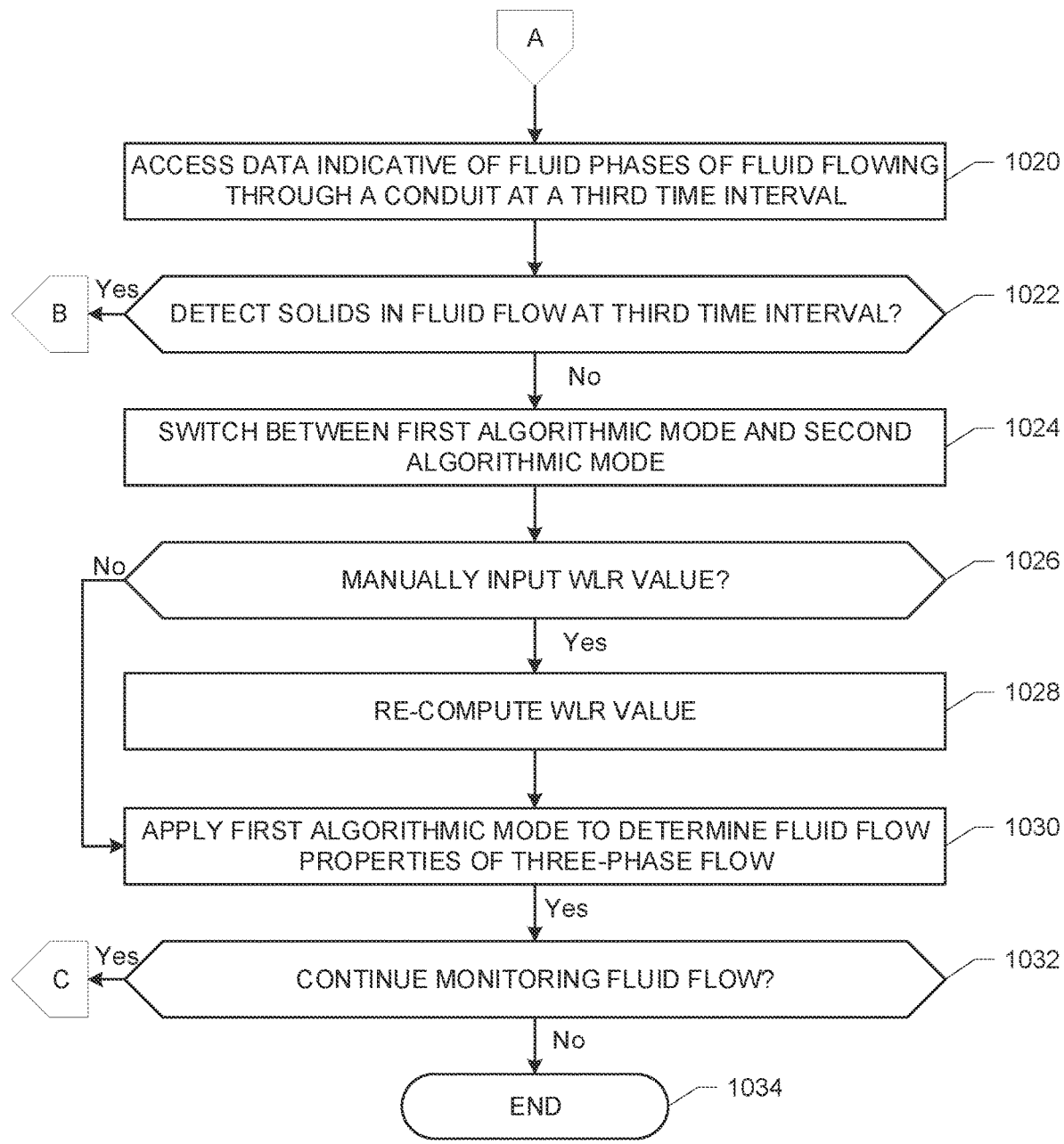

A flowchart representative of example hardware logic, machine readable instructions, hardware implemented state machines, and/or any combination thereof that may be used to implement the example flow rate analyzer 112 of FIGS. 1, 6, and 7 is shown in FIGS. 10A and 10B. The machine readable instructions may be an executable program or portion of an executable program for execution by a computer processor such as the processor 1112 shown in the example processor platform 1100 discussed below in connection with FIG. 11. The program may be embodied in software stored on a non-transitory computer readable storage medium such as a CD-ROM, a floppy disk, a hard drive, a DVD, a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowchart illustrated in FIGS. 10A and 10B, many other methods of implementing the example flow rate analyzer 112 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example process of FIGS. 10A and 10B may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

FIGS. 10A and 10B include a flowchart of example method 1000 for analyzing a multiphase fluid flowing through a pipe during time intervals in which the fluid includes three phases (e.g., oil, water, and gas) and time intervals in which the fluid includes four phases (e.g., solids, oil, water, and gas). The example method 1000 of FIGS. 10A and 10B can be implemented by the example flow rate analyzer 112 of FIGS. 1, 6, and 7.

The example method 1000 of FIGS. 10A and 10B includes accessing data indicative of fluid flowing through a fluid conduit in a first time interval (block 1002). The data can be generated by, for example, the MPFM 102, 602, 702 of FIGS. 1, 6, and 7, the solid detection sensor(s) 116 of FIG. 1, and/or the sand flowmeters 616, 706 including the piezoelectric sand detector 500 of FIG. 5 as fluid flows through the fluid conduit 108, 604, 708. The data is transmitted to the flow rate analyzer 112 of FIG. 1 and stored in the database 114. The time interval can have a duration of, for example, one second.

The example method 1000 includes determining if solids (e.g., sand) are present in the fluid flow in the first time interval (block 1004). For example, the solids detector 120 of the flow rate analyzer 112 analyzes the data received from the MPFM 102, 602, 702, the solid detection sensor(s) 116, and/or the sand flowmeters 616, 706 including the sand detector 500 to determine whether solids such as sand are present in the fluid. The solids detector 120 can detect solids based on signal data meeting predefined threshold(s) (e.g., amplitude threshold(s)).

If the fluid flow does not include solids in the first time interval, the example method 1000 includes checking if the fluid flow during the preceding time interval included solids (block 1006). For example, the solids detector 120 can analyze the data previously collected for the earlier time interval and stored in the database 114. If the fluid flow in the preceding time interval included solids, the solution mode switcher 122 of the example flow rate analyzer 112 determines that an algorithmic mode (e.g., the solution triangles 200, 300, 800, 802) used by the calculator 124 of the flow rate analyzer 112 should be updated from the algorithmic mode used for four-phase fluid flows (e.g., the SLG solution triangle 300, 800) to the algorithmic mode used for three-phase fluid flows (e.g., the OWG solution triangle 200, 802). In such examples, the method 1000 includes switching between algorithmic modes to enable the calculator 124 to use the algorithmic mode for three-phase fluid flows to analyze the fluid in the first time interval (block 1008).

The example method 1000 includes applying a first algorithmic model (e.g., the OWG solution triangle 200, 802) to determine one or more fluid flow properties of the three-phase flow (block 1010). For example, the calculator 124 uses the OWG solution triangle 200, 802 and data generated by the MPFM 102, 602, 702 to determine gas, water, and oil flow rates. In some examples, the calculator 124 determines a water-in-liquid (WLR) ratio based on the data received from the MPFM 102, 602, 702 and the solid detection sensor(s) 116. In some examples, the water conductivity sensor 128, 612, 704 provides water salinity measurements that are used by the calculator 124 to correct for changes in the water-point of the OWG solution triangle due to salinity change, thereby improving the accuracy of the WLR determination. The communicator 126 of the flow rate analyzer 112 can output the values generated by the calculator 124 for presentation.

The example method 1000 includes accessing data indicative of fluid phases of the fluid flowing through the fluid conduit in a second time interval (block 1012). For example, the flow rate analyzer 112 continues to receive data from the MPFM 102, 602, 702, the water conductivity sensor 128, 612, 704, the solid detection sensor(s) 116, and/or the sand flowmeters 616, 706 including the sand detector 500 during the flow of fluid through the fluid conduit 108, 604, 708.

The example method 1000 includes determining if solids are present in the fluid flow in the second time interval (block 1014). For example, the solids detector 120 analyzes the data received in the second time interval (e.g., from the solid detection sensor(s) 116, sand detector 500) to determine if the data indicates the presence of sand in the fluid flow.

In the example of FIGS. 10A and 10B, if solids are detected in the fluid flow in the second time interval, the example method 1000 includes switching between the first algorithmic mode and the second algorithmic mode (block 1016). For example, if the solids detector 120 detects that solids are present in the fluid flow, the solution mode switcher 122 determines that the calculator 124 should use the SLG solution triangle 300, 800 to analyze the four-phase fluid.

The example method 1000 includes applying a second algorithmic model (e.g., the SLG solution triangle 300, 800) to determine one or more fluid flow properties of the four-phase flow (block 1018). For example, the calculator 124 uses the SLG solution triangle 300, 800 and data generated by the MPFM 102, 602, 702 to determine solid, gas, and liquid flow rates. In some examples, the calculator 124 determines the liquid point in the SLG solution triangle 300, 800 based the WLR value calculated by the calculator 124 using the OWG solution triangle in the first time interval. In other examples, the WLR value is manually input at the flow rate analyzer 112. Also, in some examples, the calculator 124 determines water and oil flow rates based on the liquid flow rate and the water-in-liquid (WLR) values. In some examples, the calculator 124 determines a solids-in-liquid ratio (SLR). In some examples, the water conductivity sensor 128, 612, 704 provides water salinity measurements that are used by the calculator 124 to correct for changes in the liquid-point of the SLR solution triangle due to salinity changes, thereby improving the accuracy of the WLR and SLR determinations. The communicator 126 of the flow rate analyzer 112 can output the values generated by the calculator 124 for presentation.

The example method 1000 includes accessing data indicative of fluid phases of the fluid flowing through the fluid conduit in a third time interval (block 1020) and determining whether there are solids in the fluid flow in the third time interval (block 1022). In the example of FIGS. 10A and 10B, if the solids detector 120 determines that the fluid flow in the third time interval does not include solids (i.e., solids are now absent in the fluid as compared to the second time interval), the solutions mode switcher 122 recognizes that the algorithmic mode used by the calculator 124 to analyze the fluid should be adjusted. The example method 1000 includes switching between the first and second algorithmic modes (block 1024).

The example method 1000 includes determining if the WLR value used in connection with the algorithmic mode(s) is a manually input value (block 1026). If the WLR value is a manually input value, the example method 1000 include re-computing the WLR value to account for changes in the WLR due the absence of solids in the flow (block 1028). For example, if an operating point for the fluid falls outside, for example, the gas-liquid line of the SLG solution triangle 800, the calculator 124 recognizes that the WLR values has changed in the absence of solids in the fluid. The calculator 124 iteratively moves the liquid point in the triangle to bring the operating point inside the triangle, as discussed above in connection with FIGS. 8 and 9.

The example method 1000 includes applying the first algorithmic mode to determine fluid flow properties of the three-phase flow (block 1030). For example, the calculator 124 applies the OWG solution triangle 200, 802 to determine flow rates of the fluid now having three phases.

In the example of FIGS. 10A and 10B, if no change is detected with respect to the presence of absence of solids from the fluid flow in the different time intervals (e.g., blocks 1006, 1014, 1022), the calculator 124 continues to use a particular algorithmic mode (e.g., the SLG solution triangle 300, 800, the OWG solution triangle 200, 802) until the solids detector 120 detects a change in the fluid phase composition. The example method 1000 continues to analyze the fluid with respect to phase composition and corresponding fluid properties until a decision is made to stop monitoring the fluid flow (blocks 1032, 1034).

Figure 11:
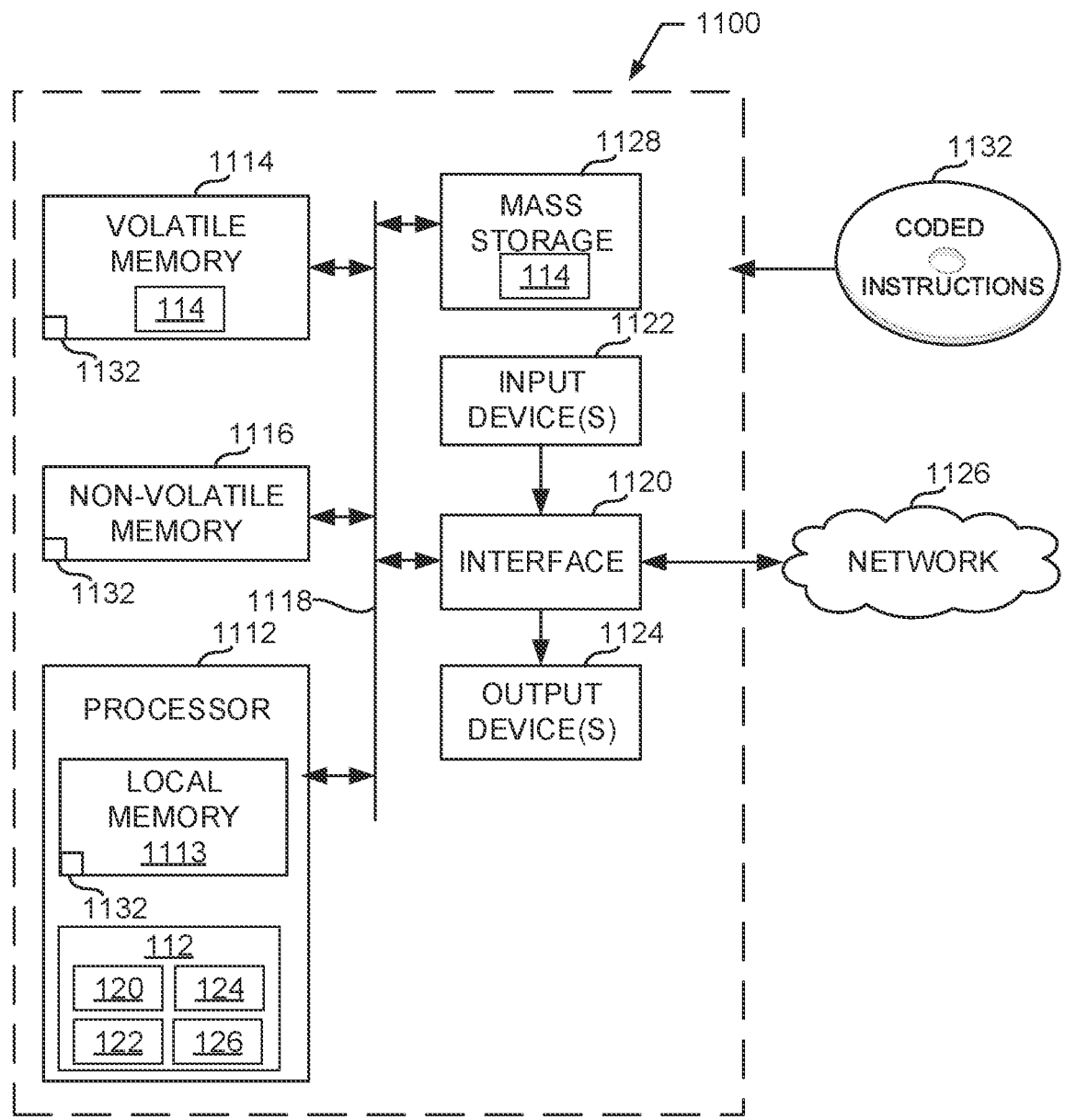
FIG. 11 is a processor platform to execute instructions to implement the method of FIGS. 10A and 10B and/or, more generally, the example flow rate analyzer of FIGS. 1, 6, and/or 7.

FIG. 11 is a block diagram of an example processor platform 1100 structured to execute the instructions to implement the method of FIGS. 10A and 10B and the flow rate analyzer 112 of FIGS. 1, 6, and/or 7. The processor platform 1100 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors, GPUs, DSPs, or controllers from any desired family or manufacturer. The hardware processor may be a semiconductor based (e.g., silicon based) device. In this example, the processor implements the example solids detector 120, the example solution mode switcher 122, the example calculator 124, and the example communicator 126.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), a Bluetooth® interface, a near field communication (NFC) interface, and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1126. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1100 of the illustrated example also includes one or more mass storage devices 1228 for storing software and/or data. Examples of such mass storage devices 1128 include floppy disk drives, hard drive disks, compact disk drives, Blu-ray disk drives, redundant array of independent disks (RAID) systems, and digital versatile disk (DVD) drives.

Coded instructions 1132 of FIG. 11 may be stored in the mass storage device 1128, in the volatile memory 1114, in the non-volatile memory 1116, and/or on a removable non-transitory computer readable storage medium such as a CD or DVD.

From the foregoing, it will be appreciated that the above-disclosed apparatus, systems, and methods provide for dynamic analysis of fluid flows including three-phases or four-phases at different intervals throughout the flow. In examples disclosed herein, a flow rate analyzer analyzes data received from sensors monitoring the fluid flow to detect whether or not solids are present in the flow. The example flow rate analyzer selectively implements a particular algorithmic mode (e.g., in the form of a solution triangle) based on the presence or absence of solids in the flow. Thus, examples disclosed herein provide for efficient analysis of four-phase fluids and/or fluids that change between three-phase and four-phase compositions over time. Examples disclosed herein adapt and extend the capabilities of multi-energy gamma-ray based multiphase flowmeters as part of analyzing flowrates of four-phase fluids. Also disclosed herein are example piezoelectric acoustic sand detectors that can be installed in a flow path of a fluid conduit to enable sand to directly impact the detectors for improved detection of solids in the fluid flow.

In the specification and appended claims: the term "coupled" is used to mean "directly coupled together" or "coupled together via one or more elements." As used herein, the terms upstream," "downstream," and other like terms indicating relative positions above or below a given point or element are used in this description to more clearly describe some embodiments of the disclosure.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

Although the preceding description has been described herein with reference to particular means, materials, and embodiments, it is not intended to be limited to the particulars disclosed herein; rather, it extends to all functionally equivalent structures, methods, and uses, such as are within the scope of the appended claims.

The invention claimed is:

1. An apparatus comprising:
a flowmeter configured to monitor each phase of a multiphase fluid flowing through a fluid conduit, wherein the multiphase fluid comprises at least water, oil, and gas;
the fluid conduit, wherein the fluid conduit is configured to provide a flow path for the multiphase fluid relative to the flowmeter;
a piezoelectric acoustic sensor coupled to the fluid conduit and configured to generate sensor data indicative of at least one of: (i) a presence of solids in the multiphase fluid during flow of the multiphase fluid through the fluid conduit or an absence of solids in the multiphase fluid during flow of the multiphase fluid through the fluid conduit, or (ii) a mass flow rate of solids in the multiphase fluid during flow of the multiphase fluid through the fluid conduit; and
a processor communicatively coupled to the piezoelectric acoustic sensor, the processor configured to:
select a first linear attenuation triangle of the flowmeter or a second linear attenuation triangle of the flowmeter, the selection being based on the sensor data of the piezoelectric acoustic sensor; and
selectively determine flow rates for the phases of the multiphase fluid based on (i) data generated by the flowmeter and (ii) the selected first linear attenuation triangle of the flowmeter or second linear attenuation triangle of the flowmeter.

2. The apparatus of claim 1, wherein the piezoelectric acoustic sensor is disposed in the flow path of the fluid conduit.

3. The apparatus of claim 2, wherein the piezoelectric acoustic sensor is disposed downstream of the flowmeter.

4. The apparatus of claim 1, further comprising a water conductivity sensor configured to generate data indicative of a change in salinity of the water in the multiphase fluid during flow of the multiphase fluid through the fluid conduit.

5. The apparatus of claim 1, wherein if the sensor data indicates the absence of solids in the multiphase fluid, the processor is configured to determine an oil flow rate value, a water flow rate value, and a gas flow rate value of the multiphase fluid based on the first linear attenuation triangle of the flowmeter.

6. An apparatus, comprising:
a flowmeter;
a fluid conduit configured to provide a flow path for a fluid relative to the flowmeter;
a sensor coupled to the fluid conduit and configured to generate sensor data indicative of at least one of: (i) a presence of solids in the fluid during flow of the fluid through the fluid conduit or an absence of solids in the fluid during flow of the fluid through the fluid conduit, or (ii) a mass flow rate of solids in the fluid during flow of the fluid through the fluid conduit; and
a processor communicatively coupled to the sensor, the processor configured to selectively determine flow rates for one or more phases of the fluid based on data generated by (i) the flowmeter and (ii) a first algorithmic mode or a second algorithmic mode selected based on the sensor data, wherein if the sensor data indicates the presence of solids in the fluid, the processor is configured to determine a solid flow rate value, a gas flow rate value, and a liquid flow rate value based on the second algorithmic mode.

7. The apparatus of claim 6, wherein the processor is further configured to determine a water flow rate value and an oil flow rate value based on the liquid flow rate value and a water-in-liquid ratio value.

8. A method comprising:
monitoring, using a flowmeter, each phase of a multiphase fluid flowing through a fluid conduit, wherein the multiphase fluid comprises at least water, oil, and gas;
generating, using a piezoelectric acoustic sensor, sensor data indicative of at least one of: (ii) a presence of solids in the multiphase fluid during flow of the multiphase fluid through the fluid conduit or an absence of solids in the multiphase fluid during flow of the multiphase fluid through the fluid conduit, or (ii) a mass flow rate of solids in the multiphase fluid during flow of the multiphase fluid through the fluid conduit;
receiving, at a processor, the sensor data;
automatically selecting, by the processor, a first linear attenuation triangle of the flowmeter or a second linear attenuation triangle of the flowmeter, the selection being based on the sensor data;
receiving, at the processor, flowmeter data of each of the phases of the multiphase fluid, the flowmeter data generated during the flow of the multiphase fluid through the fluid conduit; and determining, by the processor, flow rates of the phases of the multiphase fluid based on (i) the flowmeter data and (ii) the selected first linear attenuation triangle of the flowmeter or second linear attenuation triangle of the flowmeter.

9. The method of claim 8, further comprising, if the sensor data is indicative of the presence or the mass flow rate of solids in the multiphase fluid, determining a value of a solids-in-liquid ratio for the multiphase fluid.

10. The method of claim 8, wherein the sensor data comprises first sensor data generated for a first time interval, the first sensor data being indicative of at least one of: the presence of solids in the multiphase fluid or the mass flow rate of solids in the multiphase fluid, wherein the determining the flow rates comprises determining first flow rates for the first time interval based on the first linear attenuation triangle of the flowmeter, and wherein the method further comprises:
 accessing second sensor data generated for a second time interval after the first time interval, the second sensor data being indicative of the absence of solids in the multiphase fluid;
 switching from the first linear attenuation triangle of the flowmeter to the second linear attenuation triangle of the flowmeter based on the second sensor data; and
 determining the flow rates of the phases of the multiphase fluid based on the second linear attenuation triangle of the flowmeter for the second time interval.

11. The method of claim 8, wherein the sensor data comprises first sensor data generated for a first time interval, the first sensor data being indicative of the absence of solids in the multiphase fluid, and wherein the method further comprises:
 determining a value of a water-in-liquid ratio of the multiphase fluid for the first time interval;
 accessing second sensor data generated for a second time interval after the first time interval, the second sensor data being indicative of at least one of; the presence of solids in the multiphase fluid or the mass flow rate of solids in the multiphase fluid; and
 using the water-in-liquid ratio to determine at least one of; a water flow rate value or an oil flow rate value for the multiphase fluid for the second time interval.

12. The method of claim 8, further comprising adjusting a value of a water-in-liquid ratio value based on a change in sensor data indicative of the absence of solids in the multiphase fluid.

13. The method of claim 8, wherein the first linear attenuation triangle of the flowmeter and the second linear attenuation triangle of the flowmeter include respective linear attenuation triangles for the multiphase fluid including three phases and the multiphase fluid including four phases.

14. The method of claim 13, further comprising determining a liquid point in the second linear attenuation triangle during flow of the multiphase fluid through the fluid conduit.

15. The method of claim 14, further comprising:
 accessing water conductivity sensor data generated by a water conductivity sensor coupled to the fluid conduit, the water conductivity sensor data being indicative of a change in salinity of water in the multiphase fluid; and
 adjusting a water point in the first linear attenuation triangle or the liquid point in the second linear attenuation triangle based on the water conductivity sensor data.

16. An apparatus comprising:
 means for generating fluid flow data for each phase of a multiphase fluid during flow of the multiphase fluid flowing through a fluid conduit, wherein the multiphase fluid comprises at least water, oil, and gas;
 means for generating sensor data indicative of at least one of: (i) presence of solids in the multiphase fluid during flow of the multiphase fluid through the fluid conduit or an absence of solids in the multiphase fluid during flow of the multiphase fluid through the fluid conduit, or (ii) a mass flow rate of solids in the multiphase fluid during flow of the multiphase fluid through the fluid conduit;
 means for selecting a first linear attenuation triangle or a second linear attenuation triangle, the selection being based on the sensor data; and
 means for determining flow rates of the phases of the multiphase fluid based on (i) the fluid flow data, (ii) the sensor data, and (iii) the selected first linear attenuation triangle or second linear attenuation triangle.

17. The apparatus of claim 16, wherein the means for generating sensor data is disposed in a flow path of the fluid conduit.

18. The apparatus of claim 17, wherein the means for generating sensor data is disposed in the fluid conduit substantially perpendicular to a flow direction of the multiphase fluid.

19. The apparatus of claim 17, wherein the means for generating sensor data is disposed downstream of the means for generating fluid flow data.

* * * * *